US011219656B2

(12) United States Patent
Choi et al.

(10) Patent No.: US 11,219,656 B2
(45) Date of Patent: Jan. 11, 2022

(54) **METHOD OF USING COMPOSITION CONTAINING *HOVENIA DULCIS* THUNB. EXTRACT AS ACTIVE INGREDIENT FOR PREVENTION AND TREATMENT OF BONE DISEASES**

(71) Applicant: Industry-Academic Cooperation Foundation, Yonsei University, Seoul (KR)

(72) Inventors: Kang Yell Choi, Seoul (KR); Pu Hyeon Cha, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 348 days.

(21) Appl. No.: 16/111,527

(22) Filed: Aug. 24, 2018

(65) Prior Publication Data

US 2018/0360901 A1    Dec. 20, 2018

Related U.S. Application Data

(62) Division of application No. 14/758,053, filed as application No. PCT/KR2012/002366 on Mar. 30, 2012, now abandoned.

(30) Foreign Application Priority Data

Mar. 31, 2011   (KR) .................... 10-2011-0029828
Mar. 9, 2012    (KR) .................... 10-2012-0024525
Mar. 9, 2012    (KR) .................... 10-2012-0024550

(51) Int. Cl.
| | |
|---|---|
| *A61K 36/71* | (2006.01) |
| *A61K 36/00* | (2006.01) |
| *A61K 36/72* | (2006.01) |
| *A23L 33/105* | (2016.01) |
| *A61K 31/235* | (2006.01) |
| *A61K 31/353* | (2006.01) |

(52) U.S. Cl.
CPC ............ *A61K 36/72* (2013.01); *A23L 33/105* (2016.08); *A61K 31/235* (2013.01); *A61K 31/353* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,261,565 B1 | 7/2001 | Empie et al. | |
| 2010/0273706 A1* | 10/2010 | Li ........................ | A61P 19/10 514/8.8 |
| 2011/0130355 A1* | 6/2011 | Du ........................ | A61P 19/02 514/25 |
| 2011/0275410 A1* | 11/2011 | Caffey ................. | A61M 5/14593 455/557 |
| 2012/0108763 A1 | 5/2012 | Vergelati et al. | |
| 2013/0136836 A1 | 5/2013 | Putter et al. | |

FOREIGN PATENT DOCUMENTS

| | | | |
|---|---|---|---|
| CN | 101518351 A | * | 9/2009 |
| GN | 101200736 A | | 6/2008 |
| KR | 100399374 B1 | | 10/2003 |
| KR | 100720026 B1 | | 5/2007 |

OTHER PUBLICATIONS

Andl et al. "WNT Signals Are Required for the Initiation of Hair Folicle Development", Developmental Cell, vol. 2, 643-653 (May 2002).
Boyden et al. "High Bone Density Due to a Mutation in LDL-Receptor-Related Protein 5", The New England Journal of Medicine, vol. 346(20): 1513-1521 (May 16, 2002).
Carthy et al. "Wnt3a Induces Myofibroblast Differentiation by Upregulating TGF-β Signaling Through SMAD2 in a β-Catenin-Dependent Manner", PLoS ONE, vol. 6(5): e19809 (May 2011).
Einhorn, T.A. "The Wnt Signaling Pathway as a Potential Target for Therapies to Enhance Bone Repair", Sci. Transl. Med. vol. 2, 42ps36 (2010).
Gong et al. "LDL Receptor-Related Protein 5 (LRP5) Affects Bone Accrual and Eye Development", Cell, vol. 107: 513-523 (Nov. 16, 2001).
Huelsken et al. "β-Catenin Controls Hair Follicle Morphogenesis and Stem Cell Differentiation in the Skin", Cell, vol. 105: 533-545 (May 18, 2001).
Johnson et al. "Linkage of a Gene Causing High Bone Mass to Human Chromosome", Am. J. Hum. Genet., vol. 60: 1326-1332 (1997).
Kennell et al. "Wnt Signaling Inhibits Adipogenesis through β-Catenin-dependent and -independent Mechanisms", The Journal of Biological Chemistry, vol. 280(25): 24004-24010 (Jun. 24, 2005).

(Continued)

*Primary Examiner* — Michael Barker
*Assistant Examiner* — Randall O Winston
(74) *Attorney, Agent, or Firm* — Mintz Levin Cohn Ferris Glovsky and Popeo, P.C.

(57) ABSTRACT

The invention relates to a composition containing extracts of the fruit of *Hovenia dulcis* Thunb., gallocatechin, and methyl vanillate as active ingredients for preventing and treating bone disease. The extracts of the fruit of *Hovenia dulcis* Thunb., the gallocatechin, and the methyl vanillate according to the present invention are natural materials and thus cause no side effects, and may activate the Wnt/β-catenin pathway to promote bone formation rather than inhibiting bone decomposition, and therefore may be effective in treating osteoporosis and related diseases. In addition, the extracts of the fruit of *Hovenia dulcis* Thunb., the gallocatechin, and the methyl vanillate according to the present invention may have the effects regrowing hair and preventing and treating wounds and metabolic diseases related to the activation of Wnt/β-catenin pathway.

2 Claims, 10 Drawing Sheets

(56) References Cited

OTHER PUBLICATIONS

Kishimoto et al. "Wnt signaling maintains the hair-inducing activity of the dermal papilla", Genes & Development, vol. 14:1181-1185 (2000).
Li et al. "Neuroprotective and Free Radical Scavenging Activities of Phenolic Compounds from Hovenia dulcis". Arch Pharm Res, vol. 28(7): 804-809 (Jul. 2005).
Little et al. "A Mutation in the LDL Receptor-Related Protein 5 Gene Results in the Autosomal Dominant High-Bone-Mass Trait", Am. J. Hum. Genet., vol. 70: 11-19 (2002).
Liu et al. "Wnt Signaling and Skeletal Development", Cell Signal, vol. 20(6): 999-1009 (Jun. 2008).
Ross et al. "Inhibition of Adipogensis by Wnt Signaling", Science, vol. 289: 950-953 (Aug. 11, 2000).
Wagner et al. "The Therapeutic Potential of the Wnt Signaling Pathway in Bone Disorders", Current Molecular Pharmacology, vol. 4: 14-25 (2011).
Yavropoulou et al. "Targeting the Wnt signaling pathway for the development of novel therapies for osteoporosis", Expert Rev. Endocrinol. Metab. 5(5): 711-722 (2010).
Yoshikawa et al. "Bioactive Constituents of Chinese Natural Medicines. III. Absolute Stereostructures of New Dihydroflavonols, Hovenitins I, II, and III, Isolated from Hoveniae Semen Seu Fructus, the Seed and Fruit of Hovenia dulcis THUNB. (*Rhamnaceae*): Inhibitory Effect on Alcohol-Induced Muscular Relaxation and Hepatoprotective Activity", Yakugaku Zasshi, vol. 117(2): 108-118 (1997).
Yoshikawa et al. "Bioactive Saponins and Glycosides. IV. Four Methyl-Migrated 16,17-seco-Dammarane Triterpene Glycosides from Chinese Natural Medicine, Hoveniae Semen Seu Fructus, the Seeds and Fruit of Hovenia dulcis THUNB.: Absolute Stereostructures and Inhibitory Activity on Histamine Release of Hovenidulciosides A1, A2, B1, and B2", Chem. Pharm. Bull. 44(9): 1736-1743 (1996).
Zhang et al. "Effect of Wnt signaling pathway on wound healing", Biochemical and Biophysical Research Communications, 378: 149-151 (2009).
Ima-Nirwana, S. et al., "Palm Vitamin E Prevents Osteoporosis in Orchidectomized Growing Male Rats", Natural Products Sciences, 6(4): 155-160 (2000) pp. 155-160.
Hong, You Lee, "Effect of Hovenia dulcis Thunb on Antioxidative Activity and the Lipid Metabolism in Rats", Dept. of Food Science & Technology Grad. School, Kangwon National University, 57 pages.
Yoshikawa, M. et al., "Bioactive Constituents of Chinese Natural Medicines. III. Absolute Stereostructures of New Dihydroflavonols, Hovenitins I, II, and III, Isolated from Hoveniae Semen Seu Fructus, the Seed and Fruit of Hovenia dulcis THUNB. (*Rhamnaceae*): Inhibitory Effect on Alcohol-Induced Muscular Relaxation and Hepatoprotective Activity", Related Articles, vol. 117 (1997) No. 2, pp. 108-118.
Ko, Chun Hay et al., "Effects of Tea Catechins, Epigallocatechin, Gallocatechin, and Gallocatechin Gallate, on Bone Metabolism", Jrl. of Agriculture and Food Chemistry, (2009) 57, pp. 7293-7297.
Li, G. et al., "Neuroprotective and free radical scavenging activities of phenolic compounds from Hovenia dulcis", Laboratory of Immunomodulator, Korea Research Institute of Bioscience and Biotechnology, http://www.ncbi.nlm.nih.gov/pubmed/16114495, dated Oct. 14, 2013, English Abstract, 1 page.
(Website article of The influence of heat on the aroma of cloudberries (*Rubus charmaemorus*) https://link.springer.com/article/10.10007/BF01123552, Mar. 1977).

* cited by examiner

METHOD OF USING COMPOSITION CONTAINING *HOVENIA DULCIS* THUNB. EXTRACT AS ACTIVE INGREDIENT FOR PREVENTION AND TREATMENT OF BONE DISEASES

CROSS-REFERENCE TO RELATED APPLICATIONS

The present application is a divisional application of U.S. application Ser. No. 14/758,053 filed on Jun. 26, 2015, which is a 371 national phase U.S. entry of International Application No. PCT/KR2012/002366 filed on Mar. 30, 2012, which claims priority to Korean Application No. 10-2011-0029828 filed on Mar. 31, 2011, Korean Application No. 10-2012-0024525 filed on Mar. 9, 2012, and Korean Application No. 10-2012-0024550 filed on Mar. 9, 2012. The applications are incorporated herein by reference.

TECHNICAL FIELD

The present invention relates to a composition containing *Hovenia dulcis* Thunb. extract as an active ingredient for the prevention and/or treatment of bone disease.

BACKGROUND

Osteoporosis refers to diseases which has no change in the chemical composition of bones and leads to a reduction of bone mass in a unit volume to lead a fracture easily, even slight shock. Most of the current therapeutic agents for osteoporosis aim at alleviating the symptoms of the diseases or preventing the progression of the diseases and thus mainly serves to delay a bone loss using an antiresorptive drug. Currently, as the therapeutic agents for osteoporosis, bisphosphonate preparations which weaken the function of osteoclasts (cells involved in bone resorption) and so prevent the bone loss are mainly used, and examples thereof include "Fosamax" by Merck & Co. and "Aktonel" by Procter Gamble Company. However, these therapeutic agents cause bones to become weak and brittle at the time of continued use as a degradation inhibitor, rather than to promote the formation of bone, and may induce additional fractures during continued use. Therefore, these may not be a fundamental therapeutical method and there remains a compulsive need to replace them. Accordingly, the functions of several types of proteins and genes associated with the formation of bone have been recently revealed. In this regard, various attempts to develop "bone formation promotor" which targets to the development of such proteins and genes have been made by the multinational pharmaceutical companies and in Korean pharmaceutical companies.

On the other hand, abnormal regulation of Wnt/β-catenin signaling pathway is associated with the development of some cancers, such as colon cancer and liver cancer. Therefore, Wnt/β-catenin signaling pathway is believed to target to the development of anti-cancer agents. In addition, the facts that mutation in Lrp5 (low-density lipoprotein receptor-related protein5), one of the receptors of Wnt protein, regulates the bone mass show that Wnt signaling pathway is associated with bone (see. Cell Signal, 2008.20: 999-1009). When the loss-of-function mutation occurs in Lrp5 genes in human (Wnt/β-catenin signaling pathway inactivation), it has been reported that a typical hereditary disease, OPPG (osteoporosis pseudoglioma syndrome) caused by a decrease in the bone mass was observed (see, Cell 2001; 107(4): 513-523.). When the gain-of-function mutation occurs in Lrp5 gene in human (Wnt/β-catenin signaling pathway activation), it has been reported that an increase in the bone mass was observed (see, Am J Hum Genet 1997; 60 (6): 1326-1332/N Engl J Med 2002; 346 (20): 1513-1521). Studies on the relevance to bone growth and density of Wnt/β-catenin signaling pathway have been actively conducted, and it has attracted attention as an effective and safe therapeutic target in the treatment of osteoporosis (see, Boyden et al. N. Engl. J. Med. 2002; Little et al. Am. J. Hum. Genet. 2002; Einhorn et al., Science Translational Medicine, 2010; Yavropoulous et al., Expert Review of Endocrinology and Metabolism, 2010, Wagner et al. Current Molecular Pharmacology, 2011).

Given these circumstances, the present inventors have conducted long-term clinical studies and experiments and discovered that the β-catenin signaling pathway can be activated using a natural product, *Hovenia dulcis* Thunb., which has substantially no side effect and is relatively inexpensive upon development as a new drug, thus leading to the present invention.

SUMMARY

The present invention was made in consideration of the above described problems, and an object of the present invention is to provide a composition for the prevention and/or treatment of bone diseases comprising a substance capable of activating the Wnt/β-catenin signaling pathway.

In order to accomplish the above object, one specific embodiment of the present invention provides a pharmaceutical composition for the prevention and/or treatment of bone diseases comprising *Hovenia dulcis* Thunb. extract as an active ingredient.

Another embodiment of the present invention provides a health functional food for the improvement and/or alleviation of bone diseases comprising *Hovenia dulcis* Thunb. extract as an active ingredient.

A further embodiment of the present invention provides a pharmaceutical composition for the prevention and/or treatment of bone diseases comprising a gallocatechin as an active ingredient.

A further embodiment of the present invention provides a health functional food for the improvement and/or alleviation of bone diseases comprising a gallocatechin as an active ingredient.

A further embodiment of the present invention provides a pharmaceutical composition for the prevention and/or treatment of bone diseases comprising a methyl vanillate as an active ingredient.

A further embodiment of the present invention provides a pharmaceutical composition for the prevention and/or treatment of alopecia comprising a methyl vanillate as an active ingredient.

A further embodiment of the present invention provides a pharmaceutical composition for wound healing comprising a methyl vanillate as an active ingredient.

A further embodiment of the present invention provides a pharmaceutical composition for the prevention and/or treatment of metabolic diseases comprising a methyl vanillate as an active ingredient.

A further embodiment of the present invention provides a health functional food for the prevention and alleviation of a bone disease, an alopecia, a wound and/or a metabolic disease comprising a methyl vanillate as an active ingredient.

A further specific embodiment of the present invention provides a cosmetic composition for the prevention and/or improvement of alopecia comprising a methyl vanillate as an active ingredient.

In the present invention, the above-described bone diseases may be characterized in that it can be selected from the group consisting of an osteoporosis, an osteomalacia, a ricket, a fibrous osteitis, an aplastic bone disease and a metabolic bone disease, but are not limited thereto. The *Hovenia dulcis* Thunb. extract, gallocatechin and methyl vanillate may be characterized in that it promotes the activity of the Wnt/β-catenin signaling pathway. The *Hovenia dulcis* Thunb. extract, gallocatechin and methyl vanillate may be, characterized in that they promote the bone formation by activating Wnt/β-catenin signaling pathway. The bone disease may be characterized in that it is osteoporosis. The dosage of *Hovenia dulcis* Thunb. extract may be characterized in that it ranges from 0.1 to 10 g/kg. The pharmaceutical composition may be characterized in that it is administered via oral, parenteral, intraarterial, intradermal, transdermal, intramuscular, intraperitoneal, intravenous or subcutaneous mutes.

In the present invention, the pharmaceutical composition for the prevention and/or treatment of alopecia may be characterized in that it is selected from the group consisting of a cream, a gel a patch, a spray, an ointment, a plaster, a lotion, a liniment, a paste or a cataplasma form. The diseases may be, characterized in that they are selected from the group consisting of telogen phase alopecia, anagen phase alopecia, anagen alopecia, traumatic alopecia, scarring alopecia or non-scarring alopecia.

In the present invention, the pharmaceutical composition for wound healing may be characterized in that it is selected from the group consisting of cream, gel, patch, spray, ointment, plaster, lotion, liniment, paste or cataplasma form. The wound may be characterized in that it is a common trauma or a bedsore.

In the present invention, the metabolic disease may be characterized in that it is selected from the group consisting of diabetes, hyperlipidemia, fatty liver, cardiovascular disease, arteriosclerosis, and obesity.

In the present invention, the term "*Hovenia dulcis* Thunb." refers to fruits or seeds having gynophore of *Hovenia dulcis* Thunb. belonging to the family of buckthorn.

In the present invention. "bone disease" results from the imbalance between osteoclasts and osteoblasts in the bone, and examples thereof include, but are not limited to, damage to the bone that is caused by a bone metastasis of cancer, an osteoporosis, an osteomalacia, a ricket, a fibrous osteitis, an aplastic bone disease and a metabolic bone disease (see, Korean patent no. 10-0399374 and 10-0720026).

The Wnt/β-catenin signaling pathway of the present invention, in addition to the relevance to the regulation of bone growth and density, are associated with a hair growth, a wound healing and a fatty differentiation (metabolic disease).

It has been reported that Wnt/β-catenin signaling pathway promotes the formation of the hair follicle (WNT signals are required for the initiation of hair follicle development Andl T, et al (2002) Dev Cell. 2: 643-653.); it plays an important role to maintain and activate the genes expressed during the growth phase of the hair cycle (Wnt signaling maintains the hair-inducing activity of the dermal papilla. Kishimoto J, et al. (2000) Genes Dev 14: 1181-1185); and it promotes differentiation from stem cells into keratinocytes (β-catenin controls hair follicle morphogenesis and stem cell differentiation in the skin. Huelsken J, et al (2001) Cell 105: 533-545).

In addition, it has been reported that Wnt/β-catenin signaling pathway enhances the wound healing via activation of TGF-β signaling pathway (Effect of Wnt signaling pathway on wound healing. Zhang D L, et al. (2009) Biochem Biophys Res Commun. 378: 149-151), and promotes the formation of myofibroblasts, known as a key regulator in the course of wound healing (Wnt3a Induces Myofibroblast Differentiation by Upregulating TGF-β Signaling Through SMAD2 in a β-Catenin-Dependent Manner. Jon M C, et al (2011) Plos ONE. 6: e19809). Finally, Wnt signaling pathway has been known to inhibit the differentiation of fat from adipose precursor cells into fat through stabilization of β-catenin (Wnt Signaling Inhibits Adipogenesis through siCatenin-dependent and -independent Mechanisms Jennifer A K, et al. (2005) Wnt Signaling Inhibits Adipogenesis through siCatenin-dependent and -independent Mechanisms. J Biol Chem 280: 24004-24010). Further, Wnt signaling pathway has been reported to inhibit the differentiation of 3T3-L1 preadipocytes into fat (Inhibition of Adipogenesis by Wnt Signaling Sarah E R, et al (2000) Science 289: 950-953). The compositions of the present invention may further comprise suitable carriers, excipients and diluents which are conventionally used for the preparation of the pharmaceutical composition. The compositions of the present invention can be formulated into a powder, a granule, a tablet, a capsule, a suspension, an emulsion, a syrup, an aerosol an oral preparation, an external preparation, a suppository, and a sterile injectable solution in accordance with a conventional method, respectively. The carriers, excipients and diluents which can be included in the composition containing the extract may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrlidone, water, methyl hydroxybenzoate, propyl hydroxybenzoate, talc, magnesium stearate, and mineral oil. When the preparation is formulated, diluents or excipients such as fillers, extenders, binders, wetting agents, disintegrating agents and surfactants are normally used. Solid formulations for oral administration include tablets, pills, powders, granules, capsules and the like. These solid preparations are formulated by mixing the extract with one or more excipients, for example, starch, calcium carbonate, sucrose, lactose, gelatin and the like. In addition to a simple excipient, lubricants such as magnesium stearate or talc may also be used. The liquid preparation for oral administration may include suspensions, solutions, emulsions, and syrups. In addition to a simile diluent such as water, liquid paraffins commonly used, various excipients, for example, wetting agents, sweetening agents, flavoring agents, preservatives and the like may be included. Formulations for parenteral administration used herein include sterilized aqueous solutions, non-aqueous solvents, suspensions, emulsions, lyophilized preparations and suppositories. The non-aqueous solvents and suspensions used herein include propylene glycol polyethylene glycol, vegetable oils such as olive oil, and injectable esters such as ethyl oleate. The suppository base used herein includes witepsol, macrogol, tween 61, cacao butter, laurin butter, glycerogelatin and the like. The preferred dosage of the composition according to the present invention may vary depending on the patient's condition and weight, severity of disease, type of drug, administration mute and duration, but it can be selected appropriately by those skilled in the art. However, for the desired effect, the composition of the present invention is administered at a dose of 0.2 to 200 mg/kg a day, and preferably 2 to 100 mg/kg a day. Administration can also be conducted once a day or in portions several times a day. The above dosages are not intended to limit the scope of the invention in any aspect.

The compositions of the present invention may be administered by a variety of routes in rats, mice, domestic animals, mammals such as humans. All modes of administration may be expected, for example, the compositions can be administered by oral, rectal or intravenous, intramuscular, subcutaneous, intrauterine epidural or intracerebroventricular injections.

The compositions containing the compounds of the present invention can be variously utilized as medicines, foods and beverages for the prevention and improvement of bone diseases, wounds, alopecia and metabolic diseases. The food to which a compound of the invention can be added includes, for example, various foods, beverages, gum, tea, vitamin complexes, dietary supplements and the like. This food may be used in the form of powders, granules, tablets, capsules or beverages.

The above compound in the food or beverage of the present invention can be generally added in the amount of 0.01 to 15% by weight based on the total weight of the health food composition of the present invention. The health beverage composition can be added in a proportion of 0.02 to 5 g, preferably 0.3 to 1 g based on the amount of 100 ml.

The functional health beverage composition of the present invention contains the above compound as an essential component in the proportion indicated, and additionally it can contain various flavoring agents or natural carbohydrates as a additional component like other conventional beverages, but the liquid component is not particularly limited thereto.

Examples of the aforementioned natural carbohydrates include monosaccharides such as glucose, fructose and the like; disaccharides such as maltose, sucrose and the like; polysaccharides such as dextrin; a conventional sugar such as cyclodextrin; and a sugar alcohol such as xylitol, sorbitol, erythritol and the like. As the flavoring agents other than those described above, natural flavoring agents (thaumatin, *stevia* extract, for example, rebaudioside A, glycyrrhizin, etc.) and synthetic flavoring agents (saccharin, aspartame, etc.) can be advantageously used. The proportion of the above natural carbohydrate is generally about 1 to 20 g, preferably about 5 to 12 g, based on 100 ml of the composition of the present invention. In addition to the above, the compositions of the present invention may contain various nutrients, vitamins, minerals (electrolytes), flavoring agents such as natural flavoring agents and synthetic flavoring agents, coloring agents and enhancers (e.g., cheese, chocolate, etc.), pectic acid and its salts, alginic acid and its salts, organic acids, protective colloid thickeners, pH adjusting agents, stabilizers, preservatives, glycerin, alcohol, and carbonizing agents used for carbonated beverages. In addition, the compositions of the present invention may contain fruit flesh for preparing natural fruit juice, fruit juice beverages and vegetable beverages. These components may be used independently or in combination of two or more thereof. The proportion of these additives is not very important, but it is generally chosen in the range of 0 to about 20 parts by weight per 100 parts of the composition of the present invention.

*Hovenia dulcis* Thunb. extract, gallocatechin and methyl vanillate used in the present invention have substantially no side effects as natural compounds, activates Wnt/β-catenin signaling pathway, and promotes the formation of bone rather than the decomposition and inhibition of bone. Therefore, the *Hovenia dulcis* Thunb. extract, gallocatechin and methyl vanillate are effective in the treatment of osteoporosis and related diseases.

Further, they have the effects of preventing and treating an alopecia, a wound and/or a metabolic disease which are associated with the activation of Wnt/β-catenin signaling pathway.

DETAILED DESCRIPTION

Hereinafter, the present invention will be described in detail with reference to the following examples. However, these examples are only intended to illustrate the invention and the content of the present invention should not be construed to be limited to the examples.

Example 1

Production and Screening of *Hovenia dulcis* Thunb. Extract

Figure 1:
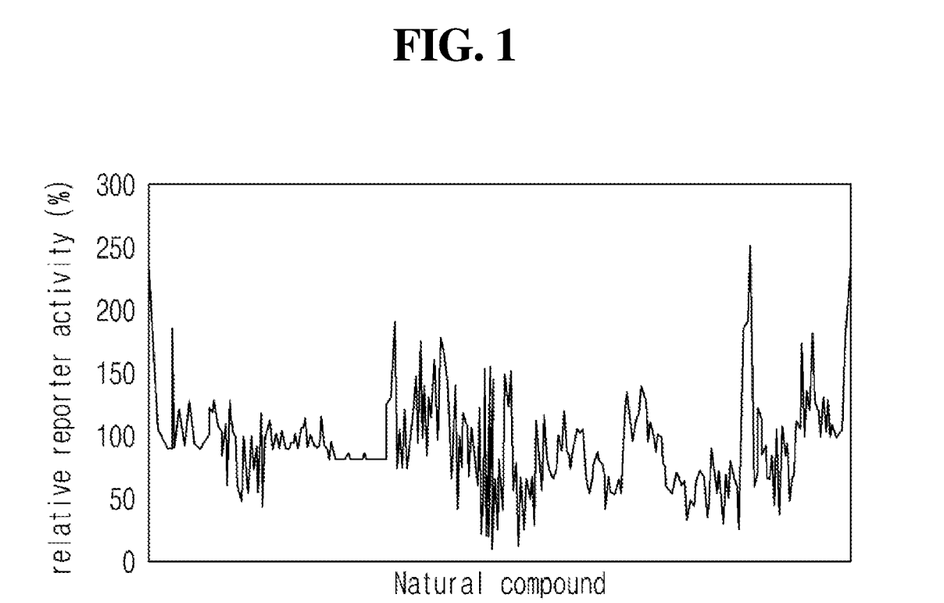
FIG. 1 shows the result of the screening of the natural compound which activates Wnt/β-catenin signaling pathway.
Figure 2:
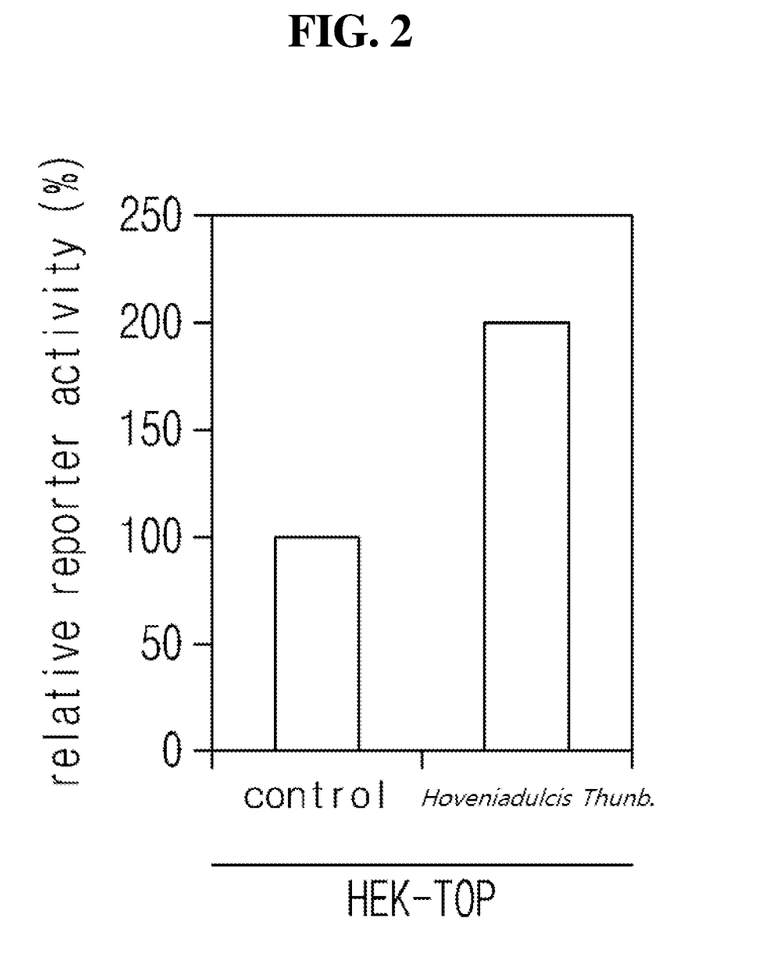
FIG. 2 shows the result of the measurement of the transcription of *Hovenia dulcis* Thunb. extract by β-catenin in HEK-TOP.

HEK-TOP is a stable cell line which has a Topflash capable of measuring the reporter of β-catenin in HEK293. The cells were treated with more than 300 natural compounds at a concentration of 1 ug/ml. After 24 hours, the transcription by β-catenin was measured via a reporter (FIG. 1). *Hovenia dulcis* Thunb. was selected as a compound which increases the transcription by β-catenin through screening. For the selected *Hovenia dulcis* Thunb., the transcription by β-catenin in HEK-TOP was measured again and the results showed that the reporter value was increased (FIG. 2). *Hovenia dulcis* Thunb. was purchased from the Korean plant extract bank and extracted using a distilled water.

Example 2

Confirmation of the Efficacy of *Hovenia dulcis* Thunb. Extract

Figure 3:
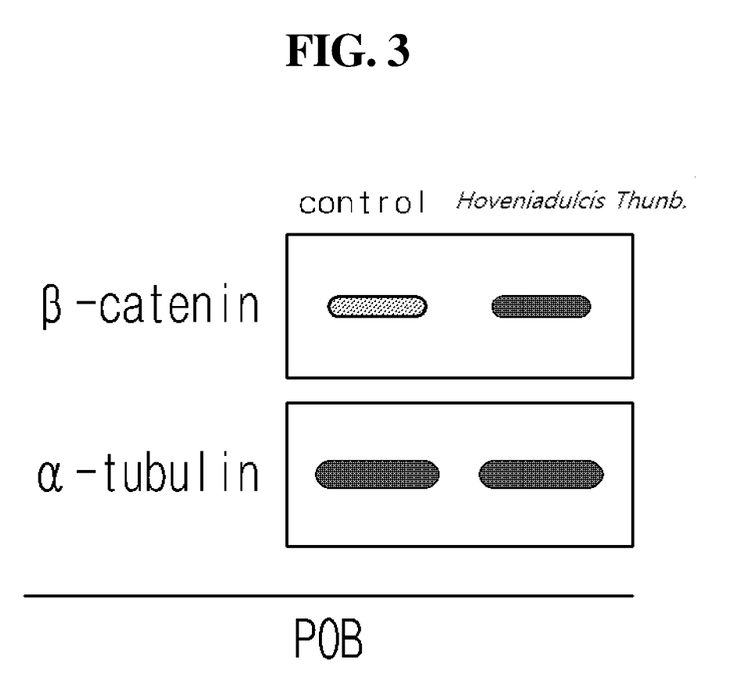
FIG. 3 is the result showing an increase of protein in β-catenin through *Hovenia dulcis* Thunb. extract.

In the calvaria of 4-day-old postnatal mice supplied by Orient Bio, POB (primary osteoblast) was separated and then treated with 5 μg/ml of *Hovenia dulcis* Thunb. extract for 24 hours. The results showed that β-catenin protein was increased FIG. 3).

Figure 4:
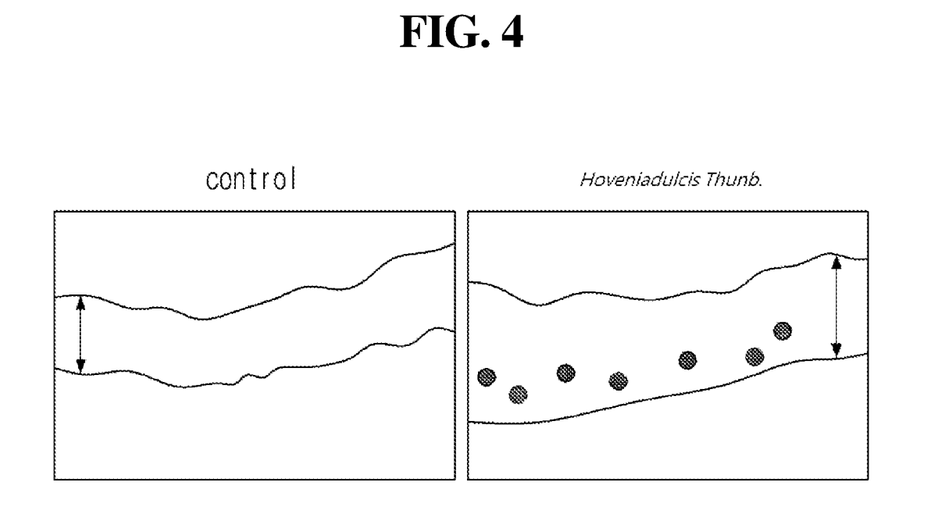
FIG. 4 is a photograph confirming an increase of β-catenin via immunohistochemical staining.
Figure 5:
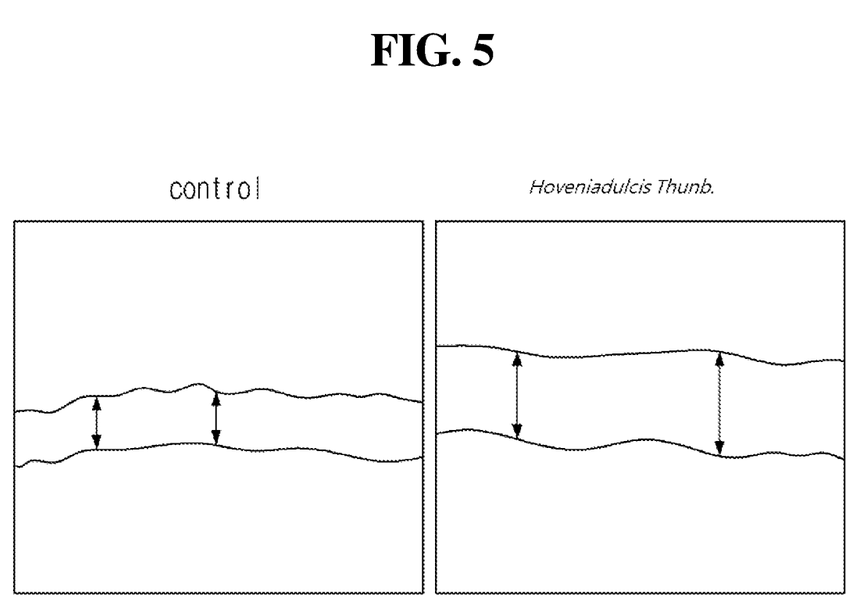
FIG. 5 is a photograph showing an increase in thickness of the calvaria of a *Hovenia dulcis* Thunb. extract-treated group.
Figure 6:
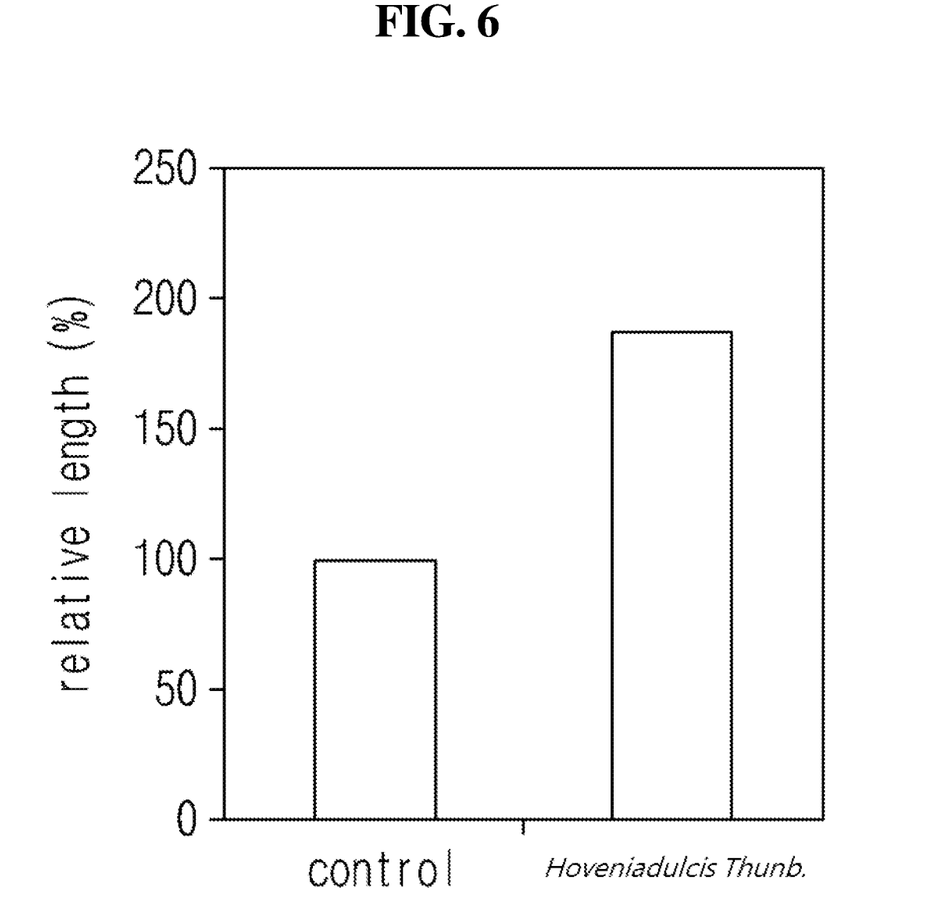
FIG. 6 is a photograph showing an increase in thickness of the calvaria of a *Hovenia dulcis* Thunb. extract-treated group.

While inducing the differentiation in the calvaria of 4-day-old postnatal rat, 5 μg/ml of *Hovenia dulcis* Thunb. extract was treated for a week. As a result, it was confirmed through the immunohistochemical staining that β-catenin was increased in the *Hovenia dulcis* Thunb. extract-treated group (FIG. 4). In addition, the results of the measurement of the thickness showed that the thickness of the calvaria was increased in the *Hovenia dulcis* Thunb. extract-treated group as compared to the control group (FIG. 5 and FIG. 6).

Example 3

Confirmation of the Efficacy of Gallocatechin and Methyl Vanillate

Gallocatechin and methyl vanillate are known as one component of *Hovenia dulcis* Thunb. extract capable of activating Wnt/β-catenin. By changing the concentrations of gallocatechin and methyl vanillate, the effects on the bone growth were investigated (Chem Pharm Bull (Tokyo), 1996 September; 44 (9): 1736-43; Yakugaku Zasshi. 1997 February; 117 (2): 108-18; Arch Pharm Res. 2005 July; 28 (7): 804-9).

Figure 7:
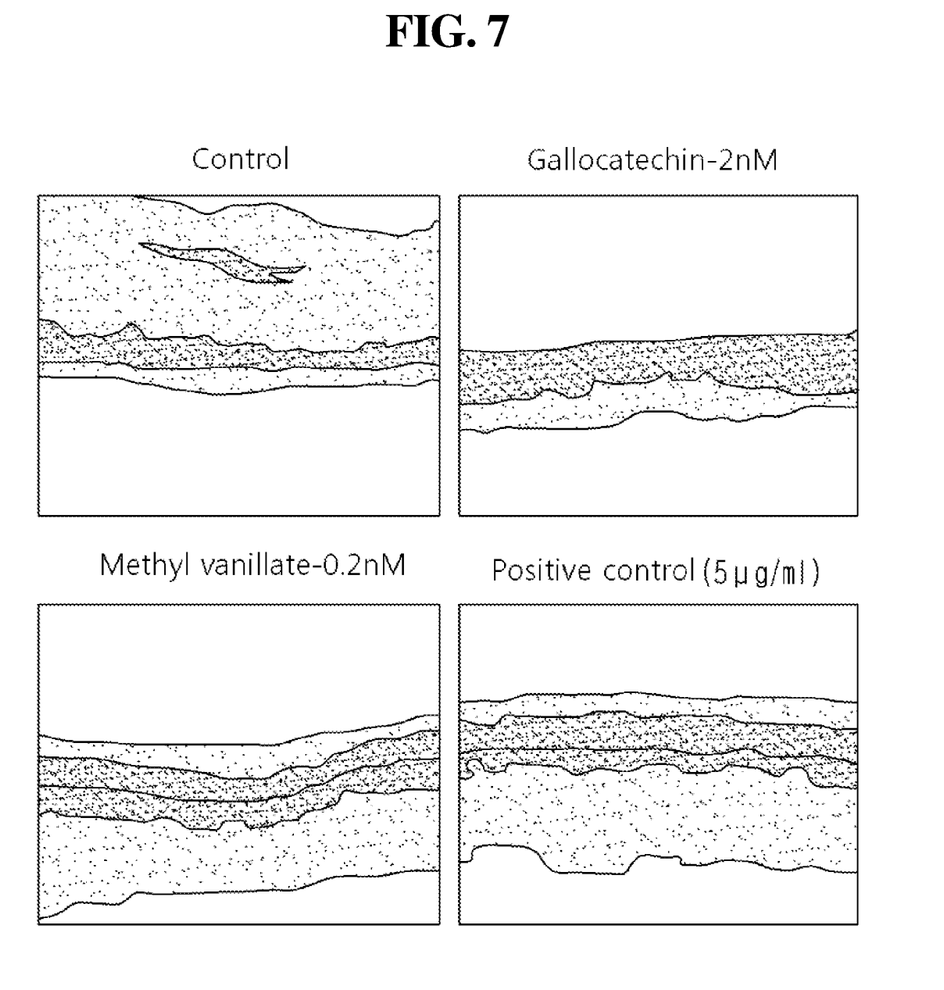
FIG. 7 is a photograph showing the growth of bone by gallocatechin and methyl vanillate.

While inducing the differentiation in the calvaria of 4-day-old postnatal mice supplied by Orient Bio. 2 nM of gallocatechin and 0.2 nM of methyl vanillate were treated for one week. The result of the measurement of the thickness showed that the thickness of the calvaria was increased in the gallocatechin and methyl vanillate-treated groups (FIG. 7). Also, it was confirmed that the thickness of the calvaria was increased in a small amount as compared to the positive control group (*Hovenia dulcis* Thunb. extract).

Figure 8:
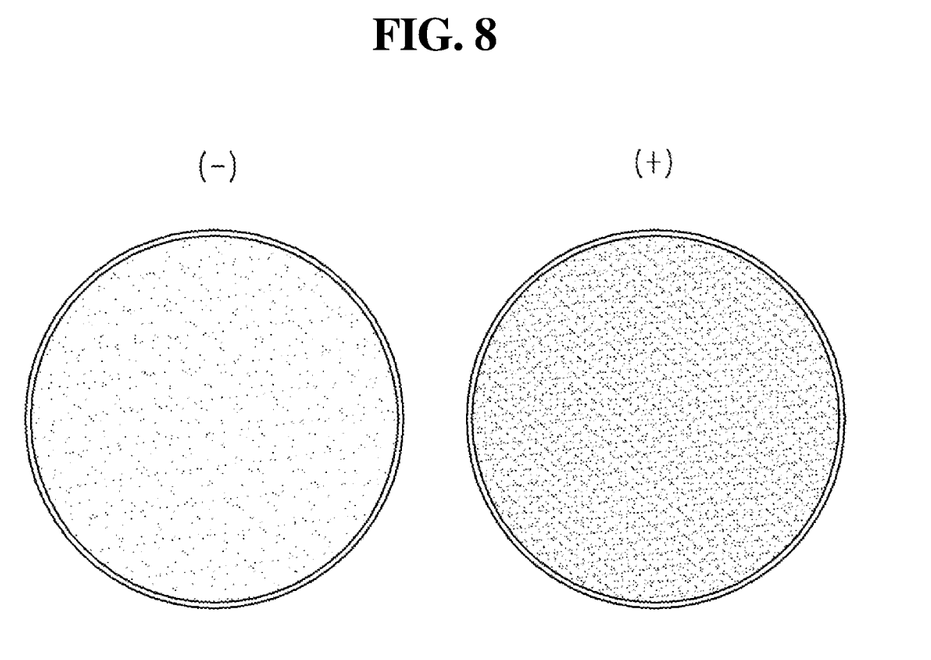
FIG. 8 is a photograph showing the induction of differentiation of POB by gallocatechin (a gallocatechin-treated group: (+), a non-treated group: (−)).
Figure 9:
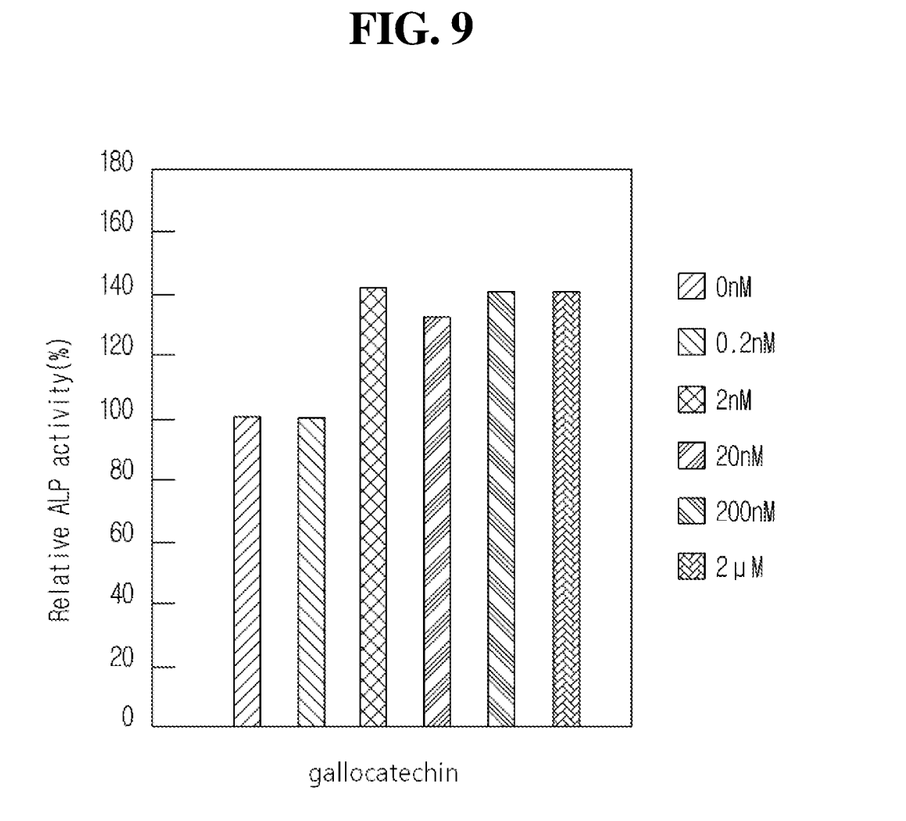
FIG. 9 and FIG. 10 are a photograph and a graph showing the effects of ALP activation of gallocatechin and methyl vanillate.
Figure 10:
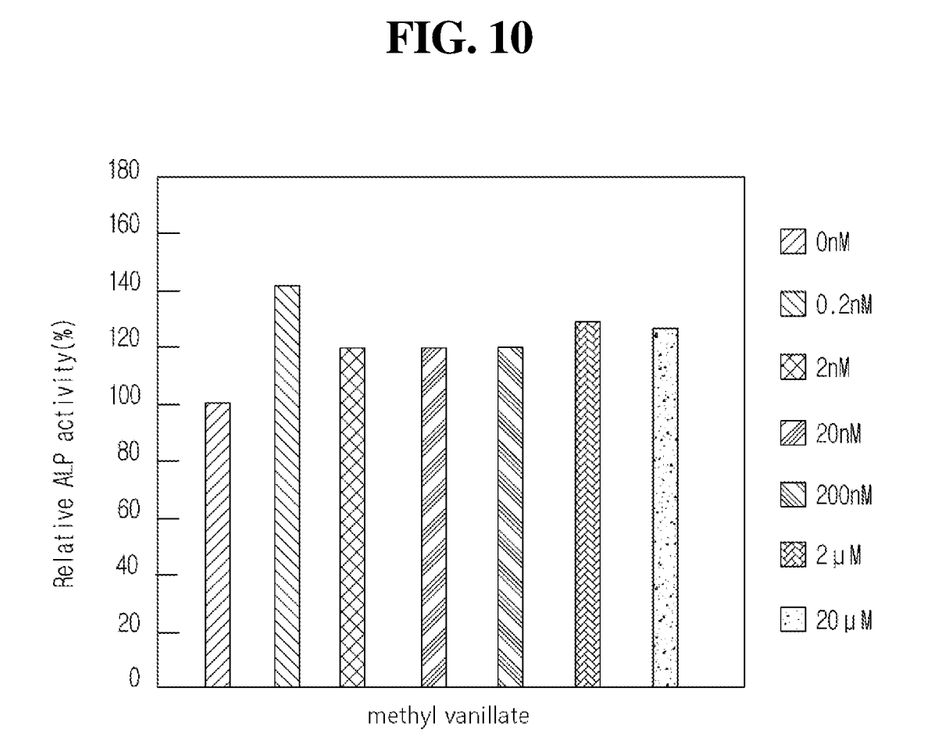

In addition, in order to confirm the activity of ALP (alkaline phosphatase) showing the activation of bones, 20 μM of gallocatechin was treated with primary osteoblast (POB) cells, and allowed to differentiate and stain for 9 days. The results showed that the expression of ALP was increased in the gallocatechin-treated group (FIG. 8). In addition, in order to confirm the activity of ALP (alkaline phosphatase) in the gallocatechin and methyl vanillate-treated groups, the analysis was conducted and the results showed that the activity of ALP was increased within the concentration gradient (FIG. 9 and FIG. 10).

Example 4

In-Vivo Administration of the Extract for the Treatment of Bone Diseases 6-week old specific pathogen-free (SPF) SD-based rat supplied from the DAEHAN Experiment Supply Center was used and the acute toxicity experiments were conducted as follows.

The *Hovenia dulcis* Thunb. extract, gallocatechin and methyl vanillate obtained in Example 1 were orally administered once at a dose of 1 g/kg to two animals in each group. The animal mortality, clinical symptoms, and change in the body weight were observed and then hematologic testing and blood biochemical tests were conducted. The autopsy was conducted and abnormalities in the thoracic and cavity organs were observed with the unaided eye. As a result of the experiments, the specific clinical symptoms and died animals were not found in all animals treated with experimental substances, Even in change in the body weight, blood tests, blood biochemical tests and autopsy findings, the toxic changes were not observed. As a result, it was confirmed that the extract of the invention showed no toxic changes up to 1 g/kg in rats, and that the minimum lethal dose ($LD_{50}$) upon oral administration was 1 g/kg or more, suggesting a safe substance.

When viewed on the basis of the above results, it has been determined that the above described *Hovenia dulcis* Thunb. extract, gallocatechin and methyl vanillate were effective in the prevention and/or treatment of a alopecia (see, WNT signals are required for the initiation of hair follicle development Andl T. et al. (2002) Dev Cell. 2: 643-653), a wound (see, Effect of Wnt signaling pathway on wound healing. Zhang D L, et al (2009) Biochem Biophys Res Commun. 378: 149-151) and a metabolic disease (Wnt Signaling Inhibits Adipogenesis through β-Catenin-dependent and -independent Mechanisms Jennifer A K, et al. (2005)) which are associated with the activity of Wnt/β-catenin signaling pathway.

The present invention was described in detail with reference to exemplary embodiments so far, but it will be understood to those skilled in the art to which the present invention pertains that various modification and changes can be made and the elements thereof can be replaced with their equivalents, without departing from the scope of the invention. Moreover, it will be possible to conduct a number of variations without departing from the essential categories of the present invention, thus applying a particular situation or material to the teachings of the present invention. Accordingly, it should be construed that the invention is not limited to the particular embodiment disclosed as the best mode that is planned to implement the present invention and that the invention includes all embodiments falling within the scope of the appended claims.

The invention claimed is:

1. A method of treating a subject having an osteoporosis, the method comprising administering a composition comprising an effective amount of methyl vanillate as an active ingredient, wherein the methyl vanillate promotes a bone formation by activating a Wnt/β-catenin signaling pathway and inducing osteoblast differentiation.

2. The method of claim 1, wherein the composition is administered via oral, parenteral, intraarterial, intradermal, transdermal, intramuscular, intraperitoneal, intravenous or subcutaneous routes.

* * * * *